United States Patent
Hwang et al.

(10) Patent No.: US 11,558,062 B2
(45) Date of Patent: Jan. 17, 2023

(54) METHODS AND APPARATUSES FOR TURNING ON AND OFF AN ADC DRIVER IN AN ULTRASOUND DEVICE

(71) Applicant: BFLY Operations, Inc., Guilford, CT (US)

(72) Inventors: Sewook Hwang, Branford, CT (US); Jungwook Yang, Newton, MA (US); Kailiang Chen, Branford, CT (US); Nevada J. Sanchez, Guilford, CT (US); Keith G. Fife, Palo Alto, CA (US)

(73) Assignee: BFLY OPERATIONS, INC., Burlington, MA (US)

( * ) Notice: Subject to any disclaimer, the term of this patent is extended or adjusted under 35 U.S.C. 154(b) by 253 days.

(21) Appl. No.: 16/937,553

(22) Filed: Jul. 23, 2020

(65) Prior Publication Data
US 2021/0028792 A1 Jan. 28, 2021

Related U.S. Application Data
(60) Provisional application No. 62/878,716, filed on Jul. 25, 2019.

(51) Int. Cl.
*H03M 1/12* (2006.01)
*A61B 8/00* (2006.01)
(Continued)

(52) U.S. Cl.
CPC .......... *H03M 1/1245* (2013.01); *A61B 8/4494* (2013.01); *A61B 8/54* (2013.01);
(Continued)

(58) Field of Classification Search
CPC ........ H03M 1/1245; H03M 1/00; H03M 1/46; A61B 8/4494; A61B 8/54; A61B 8/12;
(Continued)

(56) References Cited

U.S. PATENT DOCUMENTS

| | | |
|---|---|---|
| 4,251,743 A | 2/1981 | Hareyama |
| 8,852,103 B2 | 10/2014 | Rothberg et al. |

(Continued)

FOREIGN PATENT DOCUMENTS

| | | |
|---|---|---|
| WO | WO 2017/222964 A1 | 12/2017 |
| WO | WO 2019/099638 A1 | 5/2019 |

OTHER PUBLICATIONS

International Search Report and Written Opinion dated Nov. 2, 2020 in connection with International Application No. PCT/US2020/043286.

(Continued)

*Primary Examiner* — John W Poos
*Assistant Examiner* — Tyler J Pereny
(74) *Attorney, Agent, or Firm* — Osha Bergman Watanabe & Burton LLP

(57) ABSTRACT

Aspects of the technology described herein relate to control circuitry configured to turn on and off the ADC driver. In some embodiments, the control circuitry is configured to turn on and off the ADC driver in synchronization with sampling activity of an ADC, in particular based on when an ADC is sampling. The control circuitry may be configured to turn on the ADC driver during the hold phase of the ADC a time period before the track phase and to turn off the ADC driver during the hold phase a time period after the track phase. In some embodiments, the control circuitry is configured to control a duty cycle of the ADC driver turning on and off. In some embodiments, the control circuitry is configured to control a ratio between an off current and an on current in the ADC driver.

20 Claims, 12 Drawing Sheets

(51) Int. Cl.
  *G01S 7/52* (2006.01)
  *A61B 8/12* (2006.01)
  *H03M 1/00* (2006.01)

(52) U.S. Cl.
  CPC ............ *G01S 7/52025* (2013.01); *A61B 8/12* (2013.01); *A61B 8/4236* (2013.01); *A61B 8/4444* (2013.01); *G01S 7/5208* (2013.01); *H03M 1/00* (2013.01)

(58) Field of Classification Search
  CPC . A61B 8/4236; A61B 8/4444; G01S 7/52025; G01S 7/5208; G01S 15/8915
  See application file for complete search history.

(56) References Cited

U.S. PATENT DOCUMENTS

| | | | |
|---|---|---|---|
| 9,229,097 B2 | 1/2016 | Rothberg et al. | |
| 9,473,136 B1 | 10/2016 | Chen et al. | |
| 9,492,144 B1 | 11/2016 | Chen et al. | |
| 9,521,991 B2 | 12/2016 | Rothberg et al. | |
| 9,592,030 B2 | 3/2017 | Rothberg et al. | |
| 9,592,032 B2 | 3/2017 | Rothberg et al. | |
| 9,705,518 B2 | 7/2017 | Chen et al. | |
| 9,778,348 B1 | 10/2017 | Chen et al. | |
| 9,933,516 B2 | 4/2018 | Chen et al. | |
| 9,958,537 B2 | 5/2018 | Chen et al. | |
| 9,987,661 B2 | 6/2018 | Alie et al. | |
| 10,014,871 B2 | 7/2018 | Chen et al. | |
| 10,082,488 B2 | 9/2018 | Chen et al. | |
| 10,082,565 B2 | 9/2018 | Chen et al. | |
| 10,094,917 B2 | 10/2018 | Chen et al. | |
| 10,175,347 B2 | 1/2019 | Chen et al. | |
| 10,187,020 B2 | 1/2019 | Chen et al. | |
| 10,231,713 B2 | 3/2019 | Chen et al. | |
| 10,272,471 B2 | 4/2019 | Alie et al. | |
| 10,277,236 B2 | 4/2019 | Chen et al. | |
| 10,340,866 B2 | 7/2019 | Singh et al. | |
| 10,340,867 B2 | 7/2019 | Singh et al. | |
| 10,398,414 B2 | 9/2019 | Chen et al. | |
| 10,707,886 B2 | 7/2020 | Chen et al. | |
| 2011/0055447 A1 | 3/2011 | Costa | |
| 2015/0031999 A1 | 1/2015 | Willsie | |
| 2015/0244386 A1 | 8/2015 | El-Chammas | |
| 2015/0297193 A1 | 10/2015 | Rothberg et al. | |
| 2017/0163225 A1* | 6/2017 | Chen .................. | A61B 5/6801 |
| 2017/0281138 A1 | 10/2017 | Bao et al. | |
| 2017/0285152 A1 | 10/2017 | Bao et al. | |
| 2017/0360399 A1 | 12/2017 | Rothberg et al. | |
| 2018/0070925 A1* | 3/2018 | Chen .................. | G01S 7/52033 |
| 2018/0210073 A1 | 7/2018 | Chen et al. | |
| 2018/0321365 A1 | 11/2018 | Chen et al. | |
| 2018/0360426 A1 | 12/2018 | Singh et al. | |
| 2018/0361431 A1 | 12/2018 | Singh et al. | |
| 2018/0364200 A1 | 12/2018 | Chen et al. | |
| 2018/0364342 A1 | 12/2018 | Chen et al. | |
| 2018/0366102 A1 | 12/2018 | Ralston et al. | |
| 2018/0367110 A1 | 12/2018 | Singh et al. | |
| 2018/0367111 A1 | 12/2018 | Singh et al. | |
| 2018/0376253 A1 | 12/2018 | Lutsky et al. | |
| 2019/0000422 A1 | 1/2019 | West et al. | |
| 2019/0001159 A1 | 1/2019 | Chen et al. | |
| 2019/0069842 A1 | 3/2019 | Rothberg et al. | |
| 2019/0086525 A1 | 3/2019 | Chen et al. | |
| 2019/0140603 A1 | 5/2019 | Chen et al. | |
| 2019/0142387 A1 | 5/2019 | Chen et al. | |
| 2019/0142389 A1 | 5/2019 | Singh et al. | |
| 2019/0142391 A1 | 5/2019 | Bao et al. | |
| 2019/0261954 A1 | 8/2019 | Chen et al. | |
| 2019/0261955 A1 | 8/2019 | Chen et al. | |
| 2019/0282207 A1 | 9/2019 | Chen et al. | |
| 2019/0299251 A1 | 10/2019 | Chen et al. | |
| 2019/0336111 A1 | 11/2019 | Chen et al. | |
| 2020/0150252 A1 | 5/2020 | Chen et al. | |

OTHER PUBLICATIONS

International Preliminary Report on Patentability dated Feb. 3, 2022 for International Application No. PCT/US2020/043286.
PCT/US2020/043286, dated Feb. 11, 2020, International Search Report and Written Opinion.

* cited by examiner

METHODS AND APPARATUSES FOR TURNING ON AND OFF AN ADC DRIVER IN AN ULTRASOUND DEVICE

CROSS-REFERENCE TO RELATED APPLICATIONS

The present application claims the benefit under 35 U.S.C. § 119(e) of U.S. Patent Application Ser. No. 62/878,716, filed Jul. 25, 2019, and entitled "METHODS AND APPARATUSES FOR TURNING ON AND OFF AN ADC DRIVER IN AN ULTRASOUND DEVICE," which is hereby incorporated by reference herein in its entirety.

FIELD

Generally, the aspects of the technology described herein relate to ultrasound devices. Some aspects relate to turning on and off an analog-to-digital converter (ADC) driver in an ultrasound device.

BACKGROUND

Ultrasound probes may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect, an ultrasound device includes control circuitry and an analog-to-digital converter (ADC) driver coupled to the control circuitry, wherein the control circuitry is configured to turn on and off the ADC driver.

In some embodiments, the control circuitry is configured to turn on and off the ADC driver in synchronization with sampling activity of an ADC. In some embodiments, the control circuitry is configured to turn on and off the ADC driver based on when an ADC is sampling. In some embodiments, the control circuitry is configured to control a duty cycle of the ADC driver turning on and off. In some embodiments, the control circuitry is configured to control the duty cycle of the ADC driver turning on and off by selecting a duty cycle value from among multiple possible duty cycle values. In some embodiments, the multiple possible duty cycle values include three or more possible duty cycle values.

In some embodiments, the control circuitry is configured to control a ratio between a current in the ADC driver when the ADC driver is turned off and a current in the ADC driver when the ADC driver is turned on. In some embodiments, the control circuitry is configured to control the ratio between the current in the ADC driver when the ADC driver is turned off and the current in the ADC driver when the ADC driver is turned on by selecting the ratio from among multiple possible ratio values. In some embodiments, the multiple possible ratio values include three or more possible ratio values. In some embodiments, the control circuitry is configured to control a value of a current in the ADC driver when the ADC driver is turned on. In some embodiments, the control circuitry is configured to control a value of a current in the ADC driver when the ADC driver is turned off. In some embodiments, the control circuitry is configured to control the value of the current in the ADC driver when the ADC driver is turned off by selecting the value from among multiple possible values. In some embodiments, the multiple possible values include three or more possible values.

In some embodiments, the ADC driver includes a transistor receiving an input analog signal, a current source, and a switch coupled between the transistor and the current source, and the control circuitry is configured to turn off the ADC driver by opening the switch. In some embodiments, the ADC driver includes a transistor receiving an input analog signal, a first current source, a second current source, a first switch coupled between the transistor and the first current source, and a second switch coupled between the transistor and the second current source, and the control circuitry is configured to turn off the ADC driver by opening either the first switch, the second switch, or both the first and second switches. In some embodiments, the ADC driver includes a first transistor receiving an input analog signal, a current source, and a second transistor coupled between the transistor and the current source, and the control circuitry is configured to turn off the ADC driver by turning off the second transistor. In some embodiments, the ADC driver includes a first transistor receiving an input analog signal, a first current source, a second current source, a second transistor coupled between the first transistor and the first current source, and a third transistor coupled between the first transistor and the third current source, and the control circuitry is configured to turn off the ADC driver by turning off the second transistor, the third transistor, or both the second and third transistors. In some embodiments, the control circuitry is configured to turn off the second transistor, the third transistor, or both the second and third transistors by switching a signal at a gate of the second transistor, the third transistor, or both the second and third transistors from high to low or from low to high.

In some embodiments, the ultrasound device further includes an ADC coupled to an output of the ADC driver and configured to sample an analog ultrasound signal and convert the analog ultrasound signal to digital subsequent to sampling the analog ultrasound signal, and the control circuitry is configured to turn on and off the ADC driver by turning on the ADC driver prior to the ADC sampling the analog ultrasound signal and to turn off the ADC driver prior to the ADC converting the analog ultrasound signal. In some embodiments, the ultrasound device further includes an ADC coupled to an output of the ADC driver and configured to operate with a track phase and a hold phase, and the control circuitry is configured to turn on and off the ADC driver by turning on the ADC driver during the hold phase a first time period before the track phase and by turning off the ADC driver during the hold phase a second time period after the track phase. In some embodiments, the ultrasound device further includes the ultrasound device includes an ultrasound-on-chip.

Some aspects include a method to perform the actions that the apparatus is configured to perform.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
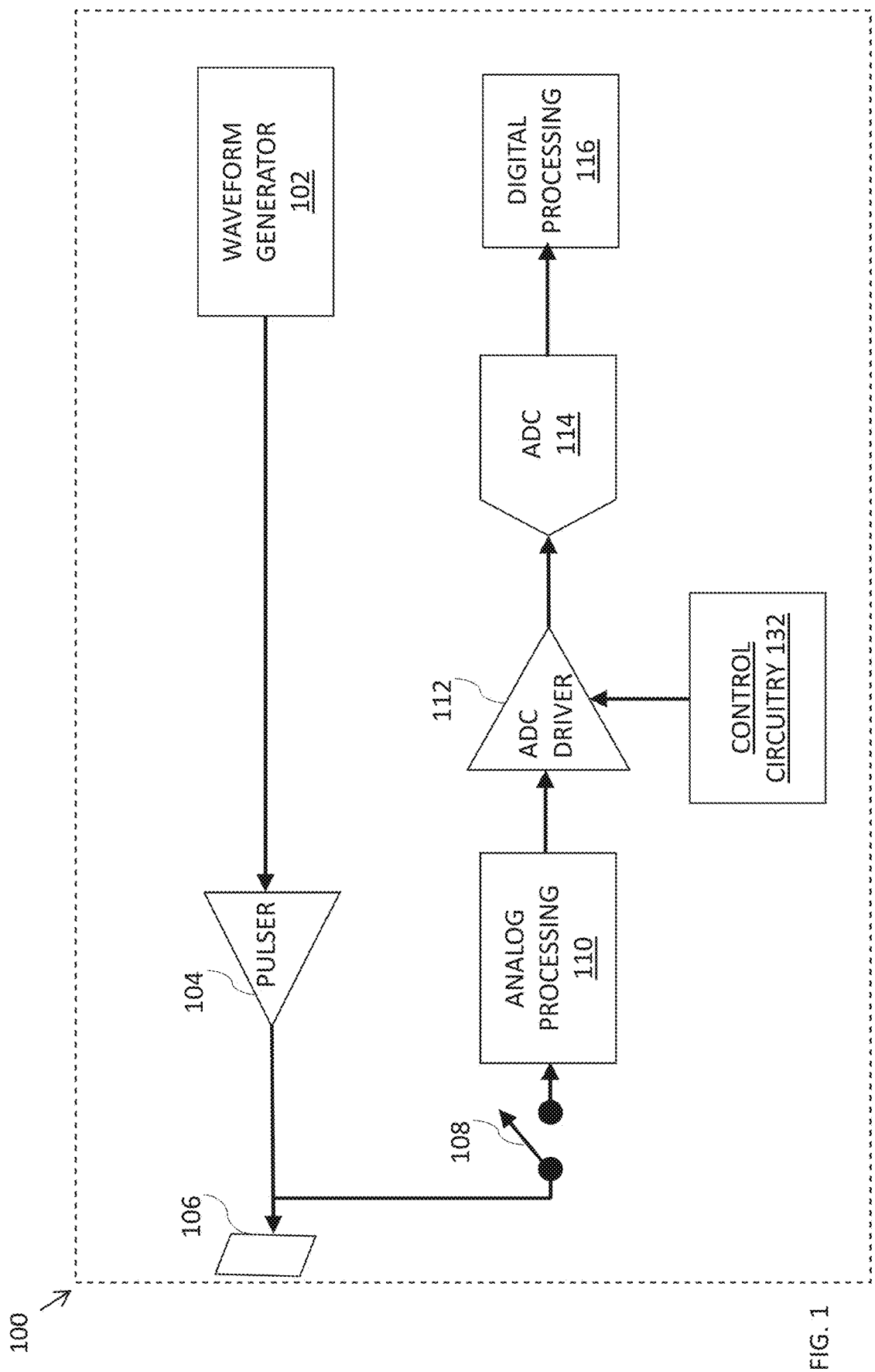
FIG. 1 illustrates an example block diagram of circuitry in an ultrasound device, in accordance with certain embodiments described herein.

Recently, ultrasound-on-chips have been developed, incorporating a large number of ultrasonic transducers and ultrasound processing units (UPU) on a single substrate. Each UPU may be a self-contained ultrasound processing unit that forms a sub-array of a complete ultrasound imaging array in a scalable fashion. Each UPU may include, for example, high-voltage pulsers to drive ultrasonic transducers to emit ultrasound; analog and mixed-signal receiver channels to receive and digitize ultrasound echoes; digital processing circuitry to filter, compress, and/or beamform the digital data from each channel; and digital sequencing circuitry to control and coordinate different parts of the circuitry to work in synchronization with one another. Such an ultrasound-on-chip can form, for example, the core of a handheld ultrasound probe. For further description of an ultrasound-on-chip, see U.S. patent application Ser. No. 15/626,711 titled "UNIVERSAL ULTRASOUND IMAGING DEVICE AND RELATED APPARATUS AND METHODS," filed on Jun. 19, 2017 and published as U.S. Pat. App. Publication No. 2017-0360399 A1 (and assigned to the assignee of the instant application), which is incorporated by reference herein in its entirety.

Certain ultrasound-on-chips may have on the order of thousands to tens of thousands of ultrasonic transducers and tens to hundreds of UPUs. The power consumed by all the circuitry on such ultrasound-on-chips may be large. Reducing power consumption of the circuitry may be helpful for reducing heating of the handheld ultrasound device in which the ultrasound-on-chip is disposed.

Certain ultrasound devices may include analog-to-digital converters (ADCs). Certain ADCs, such as successive approximation ADCs, may include a large array of switchable binary-weighted capacitors, all of which may be charged to the voltage of the input analog signal as part of the successive approximation ADC operation. Charging this capacitor array may require a large amount of current that may be provided by an ADC driver. Thus, all the ADC drivers that drive all the corresponding ADCs in the ultrasound device may consume a significant amount of power in order to provide this current. The ADC driver may provide large amounts of current to the ADC during the track phase of the ADC (when the ADC is sampling an input analog signal), but not during the hold phase of the ADC (when the ADC is converting the stored input analog signal values). Indeed, the ADC driver may not be needed for the hold phase, or portions thereof. The inventors have realized that selectively turning on and off the ADC driver may be helpful in decreasing the power consumption of the ultrasound device. In particular, the inventors and recognized that the ADC driver may be turned off for the hold phase, or portions thereof. In other words, because the ADC driver may turn on and off based on when the ADC is sampling, the ADC driver may be considered to turn off in synchronization with the ADC sampling activity. Turning on the ADC driver may mean increasing the current flowing through the ADC driver (either from zero current or a non-zero current value). Turning off the ADC driver may mean decreasing the current flowing through the ADC driver (either to zero current or to a non-zero current value).

When the current supplied to an ADC driver changes as the ADC is turned on or off, this may cause a disturbance in power supplied by the power supply. In particular, the change in dynamic current supplied to the ADC driver by the power supply may cause a voltage drop in the voltage provided by the power supply. The magnitude of this voltage drop may depend on the current in the ADC driver when it is on ("on current" or $I_{on}$) and the current in the ADC driver when it is off ("off current" or $I_{off}$). In particular, the voltage drop may be substantially equal to $(I_{on}-I_{off}) \times R_{mesh} - I_{on}(1-I_{off}/I_{on}) \times R_{mesh}$, where $R_{mesh}$ is the resistance of the power supply mesh. The inventors have recognized that power disturbance due to the ADC driver turning on and off may be controlled by enabling selection of an off/on current ratio value (i.e., $I_{off}/I_{on}$) from among multiple possible off/on current ratio values.

When an ADC driver turns on, the time for the output of the ADC driver to settle, and hence the bandwidth of the ADC driver, may depend on the on current. The inventors have recognized that the bandwidth of the ADC driver may be controlled by enabling selection of an on current value from among multiple possible on current values. Additionally, turning the ADC driver on and off around the time period when the ADC is sampling could lead to signal distortion. For example, turning on or off the ADC driver too close to the ADC sampling phase may not allow the ADC driver to settle sufficiently prior to the sampling and/or may cause the ADC driver to interfere with sampling of the input analog signal. The inventors have recognized that controlling when the ADC driver turns on and off relative to the ADC sampling, which may be equivalent to controlling the duty cycle of the ADC driver (e.g., selecting the duty cycle value from among multiple possible duty cycle values), may help with controlling signal distortion.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 illustrates an example block diagram of circuitry in an ultrasound device, in accordance with certain embodiments described herein. The ultrasound device may be an ultrasound-on-chip. For example, the circuitry of FIG. 1 may optionally be on a chip and therefore represent an ultrasound-on-chip 100, as indicated by the dashed lining. Whether on a single chip, multiple chips, or constructed as discrete components, the circuitry includes an ultrasonic transducer 106, a pulser 104, a waveform generator 102, a switch 108, analog processing circuitry 110, an analog-to-digital converter (ADC) driver 112, an analog-to-digital converter (ADC) 114, digital processing circuitry 116, and control circuitry 132.

The waveform generator 102 may be configured to provide a waveform to the pulser 104. The pulser 104 may be configured to output a driving signal corresponding to the received waveform to the ultrasonic transducer 106. When the pulser 104 is driving the ultrasonic transducer 106 (the "transmit phase"), the switch 108 may be open such that the driving signal is not applied to the analog processing circuitry 110.

The ultrasonic transducer 106 may be configured to emit pulsed ultrasonic signals into a subject, such as a patient, in response to the driving signal received from the pulser 104. The pulsed ultrasonic signals may be back-scattered from structures in the body, such as blood cells or muscular tissue, to produce echoes that return to the ultrasonic transducer 106. The ultrasonic transducer 106 may be configured to convert these echoes into electrical signals (i.e., analog ultrasound signals). When the ultrasonic transducer 106 is receiving the echoes (the "receive phase"), the switch 108 may be closed such that the ultrasonic transducer 106 may transmit the analog ultrasound signals representing the received echoes through the switch 108 to the analog processing circuitry 110.

The analog processing circuitry 110 may include, for example, one or more analog amplifiers, one or more analog filters, analog beamforming circuitry, analog dechirp circuitry, analog quadrature demodulation (AQDM) circuitry, analog time delay circuitry, analog phase shifter circuitry, analog summing circuitry, analog time gain compensation circuitry, and/or analog averaging circuitry. The analog ultrasound signal output of the analog processing circuitry 110 is outputted to the ADC driver 112.

The ADC driver 112 may be configured to buffer the analog ultrasound signals for outputting to the ADC 114. The ADC 114 may be, for example, a successive approximation ADC configured to convert analog signals to digital signals. In some embodiments, the successive approximation ADC may be a charge-redistribution successive approximation ADC that includes a charge scaling digital-to-analog converter (DAC). The charge scaling DAC may include a large array of switchable binary-weighted capacitors all of which may be charged to the voltage of the input analog signal as part of the successive approximation ADC operation. Charging this capacitor array may require a large amount of current that may be provided by the ADC driver 112. The control circuitry 132 may be configured to output control signals to the ADC driver 112. In particular, the control circuitry 132 may be configured to output control signals to the ADC driver 112 controlling turning on and off of the ADC driver 112 (as will be described further below).

The digital ultrasound signal output of the ADC 114 is outputted to the digital processing circuitry 116.

The digital processing circuitry 116 may include, for example, one or more digital filters, digital beamforming circuitry, digital quadrature demodulation (DQDM) circuitry, averaging circuitry, digital dechirp circuitry, digital time delay circuitry, digital phase shifter circuitry, digital summing circuitry, digital multiplying circuitry, requantization circuitry, waveform removal circuitry, image formation circuitry, and backend processing circuitry. The image formation circuitry may be configured to perform apodization, back projection and/or fast hierarchy back projection, interpolation range migration (e.g., Stolt interpolation) or other Fourier resampling techniques, dynamic focusing techniques, and/or delay and sum techniques, tomographic reconstruction techniques, etc.

FIG. 1 is non-limiting, and the ultrasound device may include fewer or more components than shown. For example, there may be additional components interposed between the circuitry illustrated in FIG. 1. However, even if there is, for example, more circuitry interposed between the ADC 114 and the digital processing circuitry 116, the ADC 114 may still be considered to "output" signals to the digital processing circuitry 116. In some embodiments, one waveform generator 102 may output to multiple pulsers 104 (e.g., in a multiplexed fashion). In some embodiments, one waveform generator 102 may output to only one pulser 104. In some embodiments, one pulser 104 may output to multiple ultrasonic transducers 106 (e.g., in a multiplexed fashion). In some embodiments, one pulser 104 may output to only one ultrasonic transducer 106. In some embodiments, multiple ultrasonic transducers 106 may output to one block of analog processing circuitry 110 (e.g., in a multiplexed fashion). In some embodiments, only one ultrasonic transducer 106 may output to one block of analog processing circuitry 110. In some embodiments, the ultrasonic transducer 106 may be configured to output to the ADC 114, and the analog processing circuitry 110 may be absent. In some embodiments, there may be multiple blocks of the digital processing circuitry 116, and the output of the ADC 114 may be outputted to a dedicated block of the digital processing circuitry 116. In some embodiments, there may be multiple blocks of the digital processing circuitry 116, and groups of digital signals may each be multiplexed to one of the multiple blocks of the digital processing circuitry 116. In some embodiments, all the digital signals may be multiplexed to one block of the digital processing circuitry 116. In some embodiments, there may be multiple blocks of one type of digital processing circuitry (e.g., a dedicated block for each standard binary-coded digital ultrasound signal, or a block to which a group of standard binary-coded digital ultrasound signals is multiplexed) including certain circuitry, and then all the processed signals may be multiplexed to one block of a second type of digital processing circuitry. For example, the first type of digital processing circuitry may include one or more digital filters, digital beamforming circuitry, digital quadrature demodulation (DQDM) circuitry, averaging circuitry, digital dechirp circuitry, digital time delay circuitry, digital phase shifter circuitry, digital summing circuitry, and digital multiplying circuitry, and the second type of digital processing circuitry may include requantization circuitry, waveform removal circuitry, image formation circuitry, and backend processing circuitry.

Figure 2:
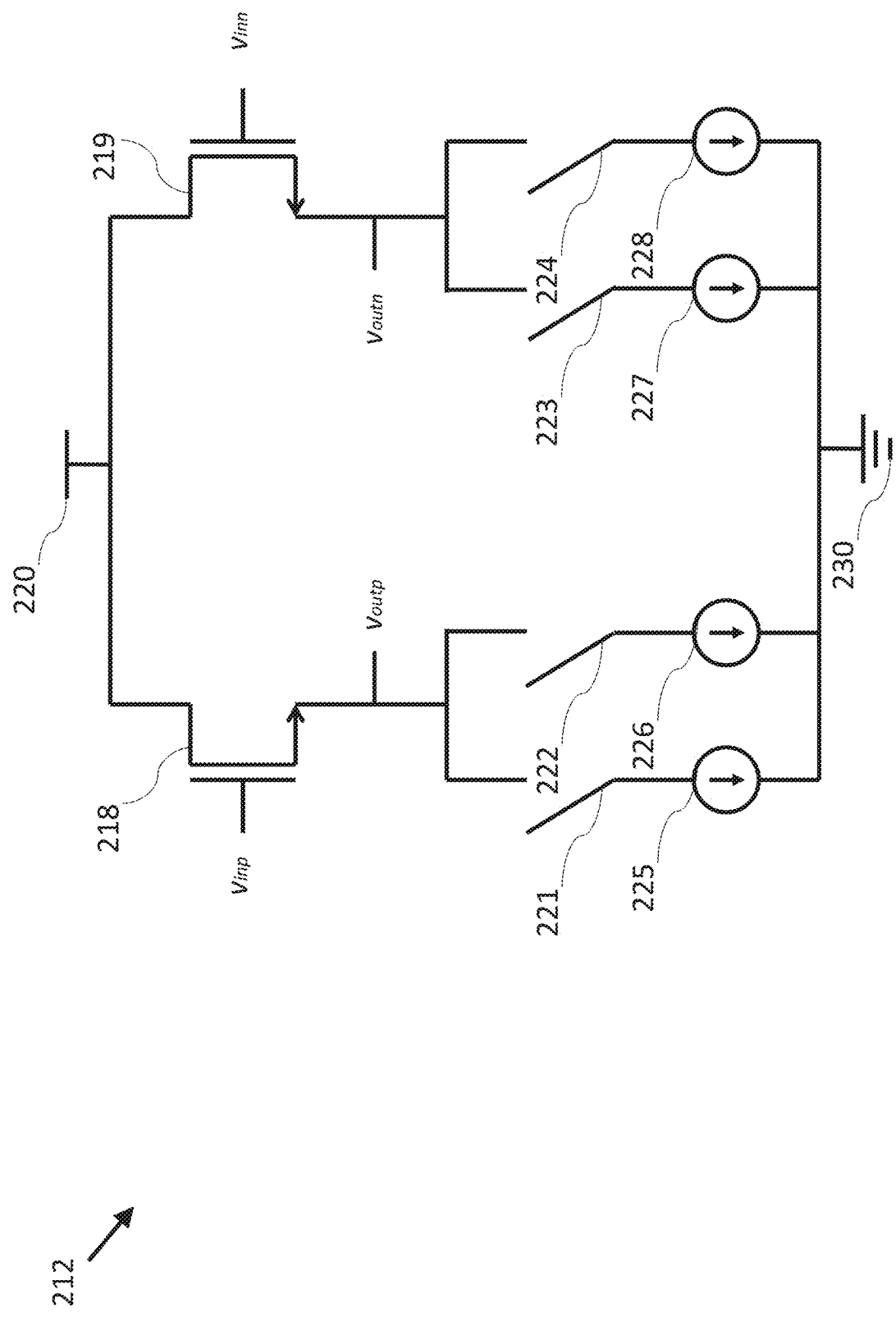
FIG. 2 illustrates an example ADC driver, in accordance with certain embodiments described herein.

FIG. 2 illustrates an example ADC driver 212, in accordance with certain embodiments described herein. The ADC driver 212 may be the ADC driver 112 illustrated in FIG. 1. The ADC driver 212 is a differential amplifier including transistors 218-219, current sources 225-228, positive power supply terminal 220, and ground terminal (ground) 230. Each of the transistors 218-224 in FIG. 2 is an n-channel metal-oxide-semiconductor field-effect transistors (nMOS). However, it should be appreciated that the ADC driver 212 may also be modified to be constructed from p-channel metal-oxide-semiconductor field-effect transistors (pMOS). The gate of the transistor 218 is coupled to a positive input signal (vinp), the drain of the transistor 218 is coupled to the positive power supply terminal 220, and the source of the transistor 218 is coupled to one terminal of each of the switches 221-222, which is also the terminal from which the positive output signal ($v_{outp}$) is taken. The gate of the transistor 219 is coupled to a negative input signal (vinn), the drain of the transistor 219 is coupled to the positive power supply terminal 220, and the source of the transistor 219 is coupled to one terminal of each of the switches 223-224, which is also the terminal from which the negative output signal ($v_{outn}$) is taken. The second terminal of each of the switches 221-222 is coupled to one terminal of the current sources 225-226, respectively. The second terminal of each of the switches 223-224 is coupled to one terminal of the current sources 227-228, respectively. The second terminal of each of the current sources 225-228 is coupled to ground 230.

The inventors have realized that selectively turning on and off the ADC driver 212 (in some embodiments, in synchronization with the sampling activity of the ADC (e.g., the ADC 114)) may be helpful in decreasing the power consumption of the ultrasound device. Turning on the ADC driver may mean increasing the current flowing through the ADC driver (either from zero current or a non-zero current value). Turning off the ADC driver may mean decreasing the current flowing through the ADC driver (either to zero current or to a non-zero current value). In operation, to turn on the ADC driver 212, switches 221-224 may be closed to enable current to flow from the current sources 225-228 to the transistors 218-219. The current flowing through the ADC driver 212 when the ADC driver 212 is turned on will be referred to as $I_{on}$. To turn off the ADC driver 212, the switches 221-224 may be opened to prevent current from flowing from the current sources 225-228 to the transistors 218-219. Alternatively, only one of the switches 221-222 may be opened and only one of the switches 223-224 may be opened, such that current may be enabled to flow from only one of the current sources 225-226 and only one of the current sources 227-228. The current flowing through the ADC driver 212 when the ADC driver 212 is turned off will be referred to as $I_{off}$. The value of $I_{off}$ may depend on which of the switches 221-224 are opened when the ADC driver 212 is turned off. As an alternative, the switches 221-224 may not be opened, such that the ADC driver 212 is not turned off (or in other words, $I_{off}=I_{on}$). Control circuitry (e.g., the control circuitry 132) may be configured to output control signals to control opening and closing of the switches 221-224. In other words, the control circuitry may be configured to control the value of $I_{off}$, and therefore be configured to control the off/on current ratio ($I_{off}/I_{on}$) from among multiple possible off/on current ratio values. For example, if the current supplied by the current sources 225 and 227 is $I_A$ and the current supplied by the current sources 226 and 228 is $I_B$, then $I_{on}$ may be $2I_A+2I_B$, and $I_{off}$ may be $2I_A$ (if the control circuitry opens the switches 222 and 224), $2I_B$ (if the control circuitry opens the switches 221 and 223), 0 (if the control circuitry opens the switches 221-224), or $2I_A+2I_B$ (if the control circuitry does not open the switches 221-224). The off/on current ratio (i.e., ($I_{off}/I_{on}$) may therefore have the following possible values, which may be selected by configuring how the control circuitry opens and closes the switches 221-224: $2I_A/(2I_A+2I_B)$, $2I_B/(2I_A+2I_B)$, 0, or 1. As a specific example, if $I_A=(3/5)*I_B$, then the possible off/on current ratios may be 37.5%, 62.5%, 100%, or 0%. It should be appreciated that the control circuitry may control the switches 221-224 to open and/or close according to a timing pattern such that the ADC driver 212 turns on and off according to a duty cycle.

When the current supplied to the ADC driver 212 varies between $I_{on}$ and $I_{off}$, this may cause a disturbance in power supplied by the power supply. In particular, the change in dynamic current supplied to the ADC driver 212 by the power supply may cause a voltage drop in the voltage provided by the power supply. The magnitude of this voltage drop may depend on $I_{on}$ and $I_{off}$. In particular, the voltage drop may be substantially equal to $(I_{on}-I_{off}) \times R_{mesh}=I_{on}(1-I_{off}/I_{on}) \times R_{mesh}$, where $R_{mesh}$ is the resistance of the power supply mesh. The inventors have recognized that power disturbance due to the ADC driver 212 turning on and off may be controlled by enabling control circuitry to control selection of the off/on current ratio value (i.e., ($I_{off}/I_{on}$) from among multiple possible off/on current ratio values, as described above. In FIG. 2, there may be four off/on current ratio options, however, including more current sources in the ADC driver 212 may enable more off/on current ratio options.

Control circuitry (e.g., the control circuitry 132) may also be configured to control $I_{on}$ by controlling bias circuitry (not shown in figure) for the current sources 225-228. In particular, the control circuitry may be configured to output control signals to the bias circuitry to select how much current is supplied by each of the current sources 225-228 from among multiple current values. For example, if the current supplied by the current sources 225 and 227 is $I_A$ and the current supplied by the current sources 226 and 228 is $I_B$, then by controlling the bias circuitry to selecting values for $I_A$ and $I_B$, the control circuitry may control the value of $I_{on}=2I_A+2 I_B$. When the ADC driver 212 turns on, the settling time of the ADC driver 212 (in particular, the slew rate), and hence the bandwidth of the ADC driver 212, may depend on $I_{on}$. The inventors have recognized that the bandwidth of the ADC driver 212 may be controlled by enabling control circuitry to select a value for $I_{on}$ from among multiple possible on current values. Providing more on current may decrease the settling time of the ADC driver 212 more than if less current is provided, but result in the ADC driver 212 consuming more power.

Figure 3:
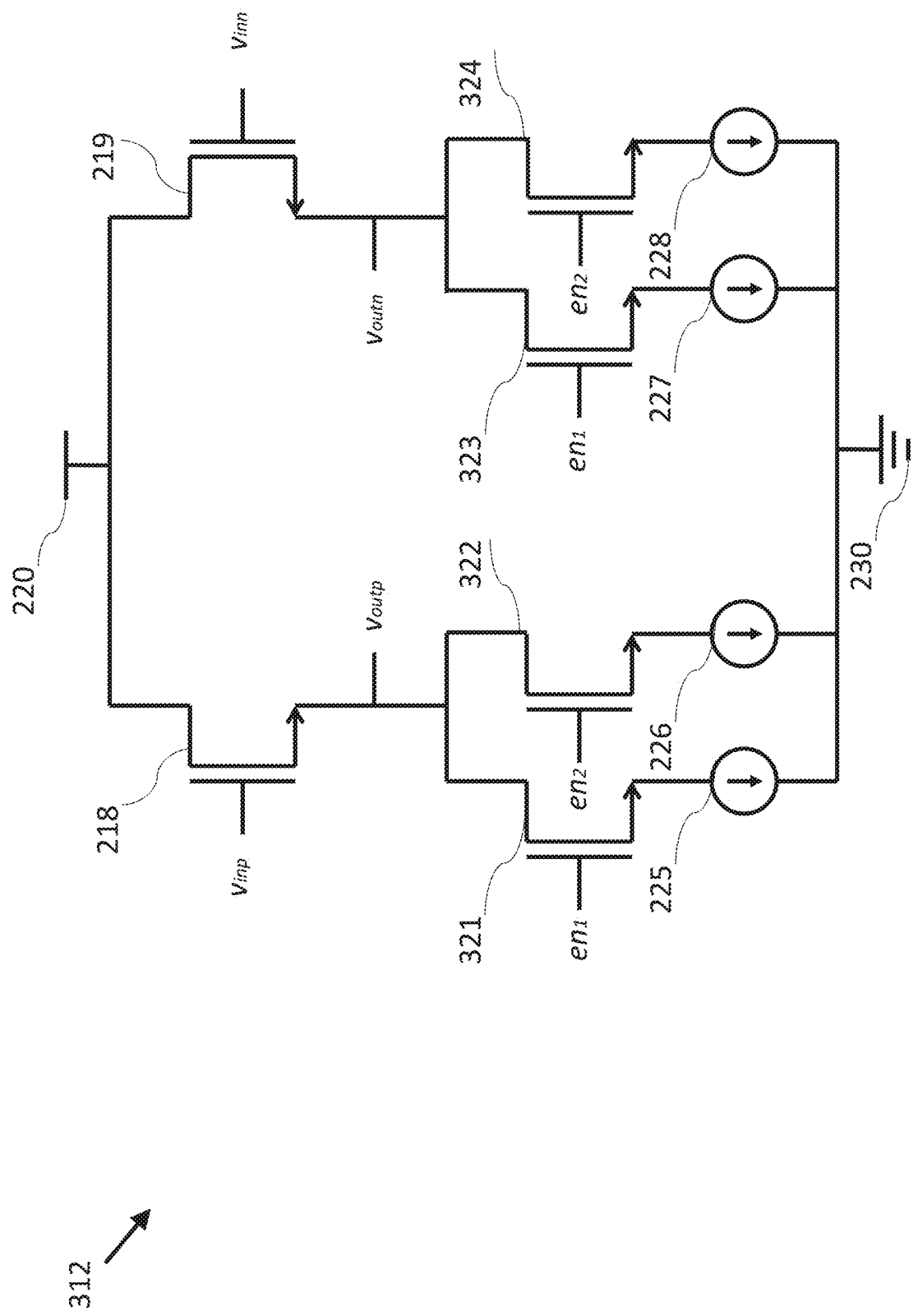
FIG. 3 illustrates an example ADC driver, in accordance with certain embodiments described herein.

FIG. 3 illustrates an example ADC driver 312, in accordance with certain embodiments described herein. The ADC driver 312 may be the ADC driver 112 illustrated in FIG. 1. The ADC driver 312 differs from the ADC driver 212 in that the switches 221-224 are replaced with transistors 321-324, respectively. Each of the transistors 321-324 in FIG. 3 is an n-channel metal-oxide-semiconductor field-effect transistors (nMOS). However, it should be appreciated that the ADC driver 312 may also be modified to be constructed from p-channel metal-oxide-semiconductor field-effect transistors (pMOS), if, for example, the transistors 218 and 219 are pMOS. The gate of the transistor 321 is coupled to a first enable signal ($en_1$), the drain of the transistor 321 is coupled to the source of the transistor 218 (which is also the terminal from which the positive output signal ($v_{outp}$) is taken), and the source of the transistor 321 is coupled to one terminal of the current source 225. The gate of the transistor 322 is coupled to a second enable signal ($en_2$), the drain of the transistor 322 is coupled to the source of the transistor 218, and the source of the transistor 322 is coupled to one terminal of the current source 226. The gate of the transistor 323 is coupled to the first enable signal ($en_1$), the drain of the transistor 323 is coupled to the source of the transistor 219 (which is also the terminal from which the negative output signal ($v_{outn}$) is taken), and the source of the transistor 323 is coupled to one terminal of the current source 227. The gate of the transistor 324 is coupled to the second enable signal ($en_2$), the drain of the transistor 324 is coupled to the source of the transistor 219, and the source of the transistor 324 is coupled to one terminal of the current source 228. Control circuitry (e.g., the control circuitry 132) may be configured to output the signals $en_1$ and $en_2$.

In operation, to turn on the ADC driver 212, the control circuitry 132 may be configured to drive $en_1$ and $en_2$ from low to high to turn on the transistors 321-324 and enable current to flow from the current sources 225-228 to the transistors 218-219. To turn off the ADC driver, the control circuitry 132 may be configured to drive both $en_1$ and $en_2$ from high to low to turn off the transistors 321-324 and prevent current from flowing from the current sources 225-228 to the transistors 218-219. Alternatively, the control circuitry 132 may be configured to only drive one of $en_1$ and $en_2$ from high to low such that only one of the transistors 321-322 and only one of the transistors 323-324 may be turned on, and current may be enabled to flow from only one of the current sources 225-226 and only one of the current sources 227-228. Alternatively, the control circuitry 132 may be configured to not drive either $en_1$ or $en_2$ from high to low such that the ADC driver 312 is not turned off. For example, if the current supplied by the current sources 225 and 227 is $I_A$ and the current supplied by the current sources 226 and 228 is $I_B$, then $I_{on}$ may be $2I_A+2I_B$, and $I_{off}$ may be $2I_A$ (if the control circuitry drives $en_2$ low), $2I_B$ (if the control circuitry drives $en_1$ low), 0 (if the control circuitry drives both $en_1$ and $en_2$ low), or $2I_A+2I_B$ (if the control circuitry does not drive either $en_1$ or $en_2$ low). The off/on current ratio (i.e., $I_{off}/I_{on}$) may therefore have the following possible values, which may be selected by configuring how the control circuitry drives $en_1$ and $en_2$ low: $2I_A/(2I_A+2I_B)$, $2I_B/(2I_A+2I_B)$, 0, or 1. Controlling the off/on current ratio may help to control the power disturbance due to the ADC driver 312 turning on and off, as described above. It should be appreciated that the control circuitry 132 may be configured to drive $en_1$ and/or $en_2$ high/low according to a timing pattern to cause the ADC driver 312 to turn on and off according to a duty cycle. It should also be appreciated that if the transistors 321-324 are pMOS, the control circuitry 132 may be configured to turn on the ADC driver by driving $en_1$ and $en_2$ from high to low, and may be configured to turn off the ADC driver by driving either or both of $en_1$ and $en_2$ from low to high.

FIGS. 2-3 are non-limiting, and the ADC driver may perform the same functions but include more or fewer components than shown. For example, the ADC driver may include dummy transistors coupled between certain components shown in FIGS. 2-3 for matching purposes. Additionally, there may be more switchable current sources than shown, allowing for greater control over the amount of current supplied to the ADC driver. Alternatively, there may only be two current sources in the ADC driver, one for each of the transistors 218-219. such that only one current value may flow through each of the transistors 218-219. It should be appreciated that the current sources 225-228 may be made from more transistors and other circuit components. Additionally, instead of ground 230, a negative power supply may be used. The ADC driver may also have a different amplifier architecture but still have the functionality for permitting of preventing current from flowing through the ADC driver.

Figure 4:
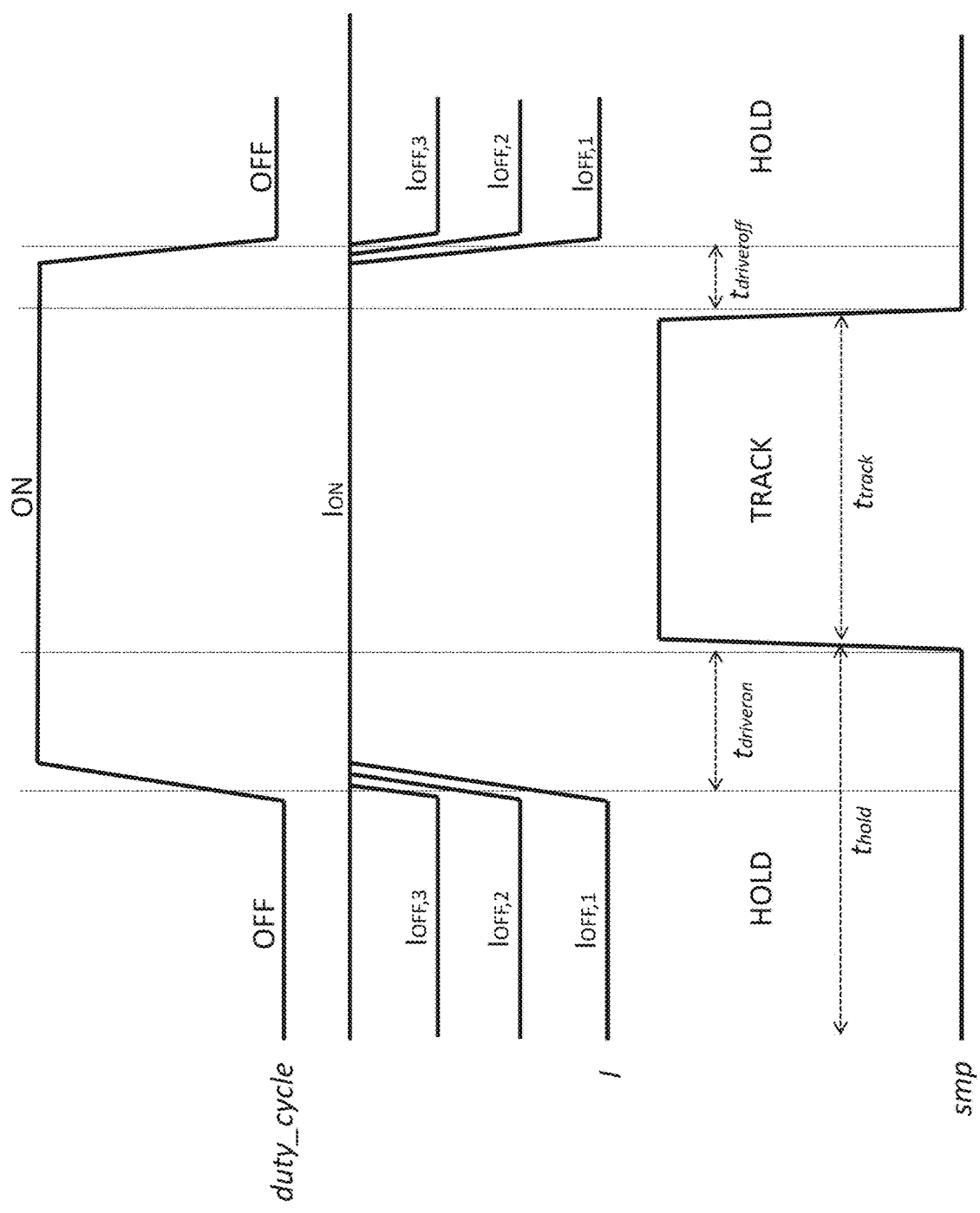
FIG. 4 illustrates an example timing diagram for an ADC driver, in accordance with certain embodiments described herein.

FIG. 4 illustrates an example timing diagram for an ADC driver, in accordance with certain embodiments described herein. The ADC driver may be, for example, the ADC drivers 112, 212, or 312. FIG. 4 illustrates timing diagrams for a signal duty_cycle, a signal smp, and a current I flowing through the ADC driver. Control circuitry (e.g., the control circuitry 132) may be configured to output the signals duty_cycle and smp and to control I as a function of time. The signal duty_cycle may be a signal controlling turning on and off the ADC driver according to a duty cycle. In FIG. 4, when duty_cycle is high, the ADC driver is on, and when duty_cycle is low, the ADC driver is off. In the example of the ADC driver 212, in some embodiments duty_cycle may be a signal controlling opening and closing of the switches 221-224. To turn on the ADC driver, duty_cycle may be driven high to close the switches 221-224, and to turn off the ADC driver, duty_cycle may be driven low to open the switches 221-224. Alternatively, duty_cycle may be a signal controlling opening and closing of one of either the switches 221 and 223 or the switches 222 and 224. To turn on the ADC driver, duty_cycle may be driven high to close either the switches 221 and 223 or the switches 222 and 224. Another signal may also be driven high to close the other switches in the ADC driver. To turn off the ADC driver, duty_cycle may be driven low to open either the switches 221 and 223 or the switches 222 and 224, while the other switches remain closed. In the example of the ADC driver 312, in some embodiments duty_cycle may be $en_1$ and $en_2$. To turn on the ADC driver, duty_cycle may be driven high to turn on the transistors 321-324. To turn off the ADC driver, duty_cycle may be driven low to turn off the transistors 321-324. In some embodiments, duty_cycle may be $en_1$. To turn on the ADC driver, duty_cycle may be driven high to turn on the transistors 321 and 323, while $en_2$ may also be driven high to turn on the transistors 322 and 324. To turn off the ADC driver, duty_cycle may be driven low to turn off the transistors 321 and 323 while $en_2$ may be kept high to keep on the transistors 322 and 324. In some embodiments, duty_cycle may be $en_2$. To turn on the ADC driver, duty_cycle may be driven high to turn on the transistors 322 and 324, while $en_1$ may also be driven high to turn on the transistors 321 and 323. To turn off the ADC driver, duty_cycle may be driven low to turn off the transistors 322 and 324 while $en_1$ may be kept high to keep on the transistors 321 and 323.

The signal smp may be a signal controlling sampling of an analog signal by an ADC (e.g., the ADC 114). In particular, in FIG. 4, the signal smp may be a signal controlling whether the ADC is tracking (i.e., sampling) the input analog signal or holding the input analog signal. In some embodiments, the ADC may be a successive approximation ADC and smp may control whether the ADC is tracking the input analog signal (e.g., coupling the input analog signal to the capacitor array of a charge scaling DAC and charging the capacitor array to the input analog signal value) or holding the input analog signal value mode (e.g., decoupling the capacitor array from the input analog signal and converting the stored input analog signal value to digital). In FIG. 4, when smp is high, the ADC is in track mode, and when smp is low, the ADC is in hold mode.

As illustrated in FIG. 4, smp is low for a time period $t_{hold}$, meaning that the ADC is in hold phase for $t_{hold}$. smp is high for a time period $t_{track}$, meaning that the ADC is in track phase for $t_{track}$. During the hold phase, duty_cycle is low (i.e., the ADC driver is off), but is switched high (i.e., the ADC driver is turned on) a time $t_{driveron}$ before the track phase begins. After the track phase ends, duty_cycle remains high for a time $t_{driveroff}$. It should be appreciated that the ADC driver may buffer the input analog signal to the ADC and provide large amounts of current to the ADC (e.g., to the capacitor array of a charge scaling DAC in the ADC) during the track phase, but not during the hold phase. Indeed, the ADC driver may not be needed for the hold phase. Accordingly, as illustrated in FIG. 4, the ADC driver is turned on during the track phase but off during the hold phase. More specifically, the ADC driver is turned off during the hold phase but turned on the time period $t_{driveron}$ before the track phase. This may help the output of the ADC driver to settle (which may occur over a settling time period) prior to the track phase beginning, so that the input analog signal is accurately stored by the ADC prior to end of the track phase. As described above, increasing the current of the ADC driver may reduce the settling time period and allow for reduction of $t_{driveron}$. In some embodiments, if $t_{track}$ is sufficiently long relative to the settling time of the ADC driver, duty_cycle may be switched high after the track phase has begun, because the output of the ADC driver may still settle to a sufficient degree prior to the end of the track phase. Additionally, the ADC driver is left on during the hold phase for a time period $t_{driveroff}$ after the track phase. This may help ensure that turning off the ADC driver does not interfere with sampling of the input analog signal during the track phase. In some embodiments, $t_{driveron}$ and $t_{driveroff}$ are the same. In some embodiments, $t_{driveron}$ and $t_{driveroff}$ are different. In some embodiments, $t_{driveron}$ is greater than $t_{driveroff}$. It should be appreciated that the ADC driver may be considered to turn off/on in synchronization with the ADC sampling activity because the ADC driver may turn on and off based on when the track phase occurs (in particular, turning on a period of time before the track phase and turning off a period of time after the track phase).

It follows from FIG. 4 that the ADC driver is on for $(t_{driveron}+t_{driveroff}+t_{track})/(t_{track}+t_{hold})\times100$ percent of the time. As will be described further below with reference to FIGS. 5-8, if the system clock of the ultrasound device has a period of $T_{sysclk}$, in some embodiments, an initial value of $t_{driveron}$ may be selected (e.g., as a multiple of $0.5T_{sysclk}$) and an initial value of $t_{driveroff}$ may be selected (e.g., as a multiple of a gate delay). The final value of $t_{driveron}$ may then be the initially selected value of $t_{driveron}$ minus $t_{driveroff}$. Thus, in such embodiments, the duty cycle of the ADC driver may be calculated as $(t_{driveron,i}+t_{track})/(t_{track}+t_{hold})\times100$ percent, where $t_{driveron,i}$ is the initially selected value for $t_{driveron}$. In some embodiments, $t_{hold}=3T_{sysclk}$, $t_{track}=T_{sysclk}$, and $t_{driveron,i}=0.5T_{sysclk}$. In such embodiments, the ADC driver may be on for 37.5% of the time (i.e., 37.5% duty cycle). This duty cycling of the ADC driver may translate to a 62.5% reduction in power consumed by the ADC driver. If, on the other hand, $t_{hold}=4T_{sysclk}$, $t_{track}=T_{sysclk}$, and $t_{driveron,i}=0.5T_{sysclk}$, then the ADC driver may be on for 30% of the time (i.e., 30% duty cycle). This duty cycling of the ADC driver may translate to a 70% reduction in power consumed by the ADC driver. The duty cycle may also be modified by modifying $t_{driveron}$ and $t_{driveroff}$. As described above, because the ADC driver may need to provide large currents to drive the capacitor array of a charge scaling DAC in the ADC, the ADC driver may contribute significantly to power consumption of the ultrasound device. Implementing turning on and off of the ADC driver according to a duty cycle may contribute to significantly decreasing the power consumption of the ultrasound device.

It should be appreciated that while FIG. 4 shows the hold phase while smp is low and the track phase while smp is high, in some embodiments the hold phase may be while smp is high and the track phase may be while smp is low. Additionally, while FIG. 4 shows that the ADC driver is turned on when duty_cycle is high and turned off when duty_cycle is low, in some embodiments, the ADC driver may be turned on when duty_cycle is low and turned off when duty_cycle is high. As described above, in some embodiments, duty_cycle may be switched to turn on the ADC driver at the beginning of the track phase, or after the track phase has begun. In some embodiments, duty_cycle may be switched to turn off the ADC driver at the end of the track phase (e.g., if interference with the track phase due to turning off the ADC driver is not a significant issue).

As illustrated in FIG. 4, the current I flowing through the ADC driver when the ADC driver is on is $I_{on}$ and the current flowing through the ADC driver when the ADC driver is off may be $I_{off,1}$, $I_{off,2}$, or $I_{off,3}$. Alternatively, the ADC driver may not cycle between being on and off, and the current flowing through the ADC driver may always be $I_{on}$. Control circuitry may select whether the current flowing through the ADC driver when the ADC driver is off is $I_{off,1}$, $I_{off,2}$, $I_{off,3}$, or $I_{on}$. Thus, the off/on current ratio may be $I_{off,1}/I_{on}$, $I_{off,2}/I_{on}$, $I_{off,3}/I_{on}$, or 1. The options in FIG. 4 may correspond to the options in FIGS. 2-3, in which the current supplied by the current sources 225 and 227 may be $I_A$, the current supplied by the current sources 226 and 228 may be $I_B$, $I_{on}=2I_A+2I_B$, and $I_{off}$ may be $2I_A$, $2I_B$, 0, or $2I_A+2I_B$. Thus, the four options for off/on current ratio may be $2I_A/(2I_A+2I_B)$, $2I_B/(2I_A+2I_B)$, 0, or 1. While FIG. 4 illustrates four off/on current ratio options, there may be more options in some embodiments (e.g., if the ADC driver includes more current sources than illustrated in FIGS. 2-3).

In some embodiments, the values of the current flowing through the ADC driver when the ADC driver is on and/or the current flowing through the ADC driver when the ADC driver is off may be zero or non-zero. Thus, it should be appreciated that according to an aspect of the application, the current may be switched from a higher current to a lower current, or vice versa, and that the application therefore provides control circuitry for controlling an input current level shift of an ADC driver.

Figure 5:
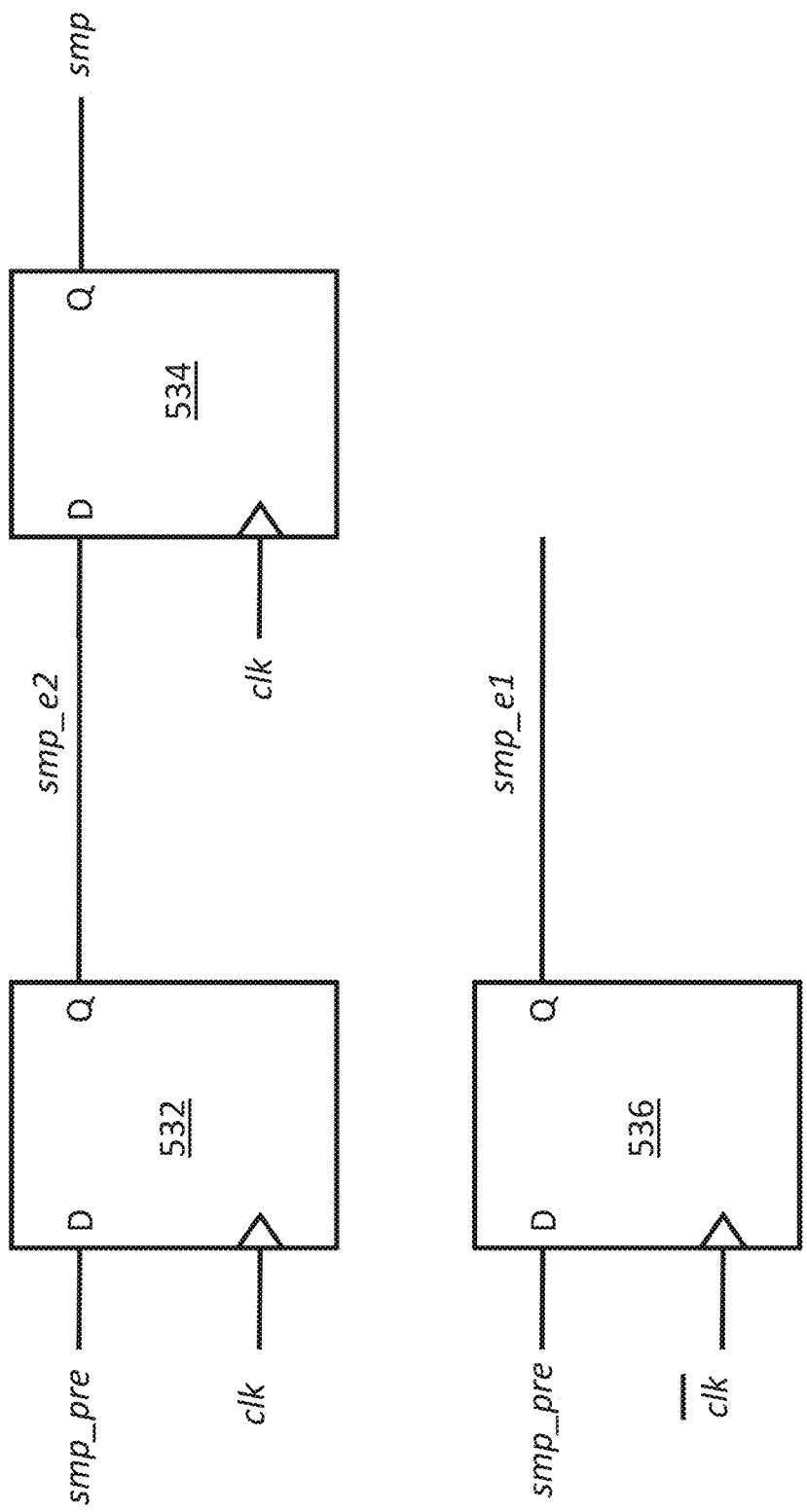
FIG. 5 illustrates example of signal generation circuitry, in accordance with certain embodiments described herein.
Figure 8:
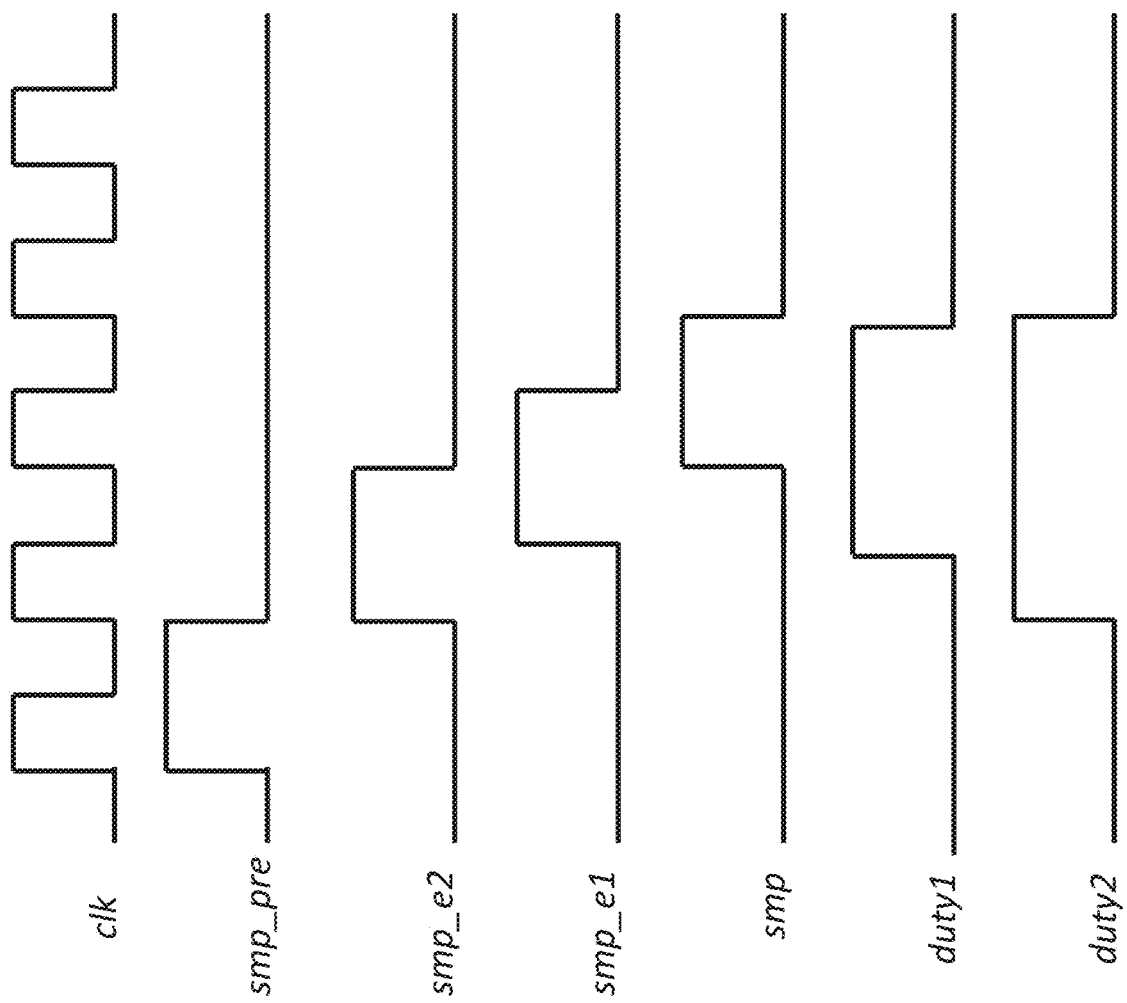
FIG. 8 illustrates example timing diagrams for signals generated by signal generation circuitry, in accordance with certain embodiments described herein.

FIG. 5 illustrates example signal generation circuitry, in accordance with certain embodiments described herein. FIG. 5 includes a flip-flop 532, a flip-flop 534, and a flip-flop 536. The flip-flops 532, 534, and 536 are D-type flip-flops, although other types of flip-flops may also be used. The signal smp_pre is coupled to the D input of the flip-flop 532. The clock signal clk is coupled to the clock input of the flip-flop 532. The signal smp_e2 is taken from the Q output of the flip-flop 532. The signal smp_e2 is coupled to the D input of the flip-flop 534. The clock signal clk is coupled to the clock input of the flip-flop 534. The signal smp is taken from the Q output of the flip-flop 534. The signal smp_pre is coupled to the D input of the flip-flop 536. The inversion of the clock signal clk is coupled to the clock input of the flip-flop 536. The signal smp_e1 is taken from the Q output of the flip-flop 536. Timing diagrams for smp_pre, smp_e2, smp_e1, smp, and clk may be found in FIG. 8. When smp_pre and clk are as illustrated in FIG. 8, in operation, the flip-flop 532 may delay the signal smp_pre by two half-clock cycles to produce the signal smp_e2, the flip-flop 534 may delay the signal smp_e2 by two half-clock cycles to produce the signal smp, and the flip-flop 536 may delay the signal smp_pre by three half-clock cycles to produce the signal smp_e1. smp_e{n} may mean that smp_e{n} is earlier by {n} half-clock cycles with respect to smp. The signal smp generated by the circuitry in FIG. 5 may be the signal smp in FIG. 4.

Figure 6:
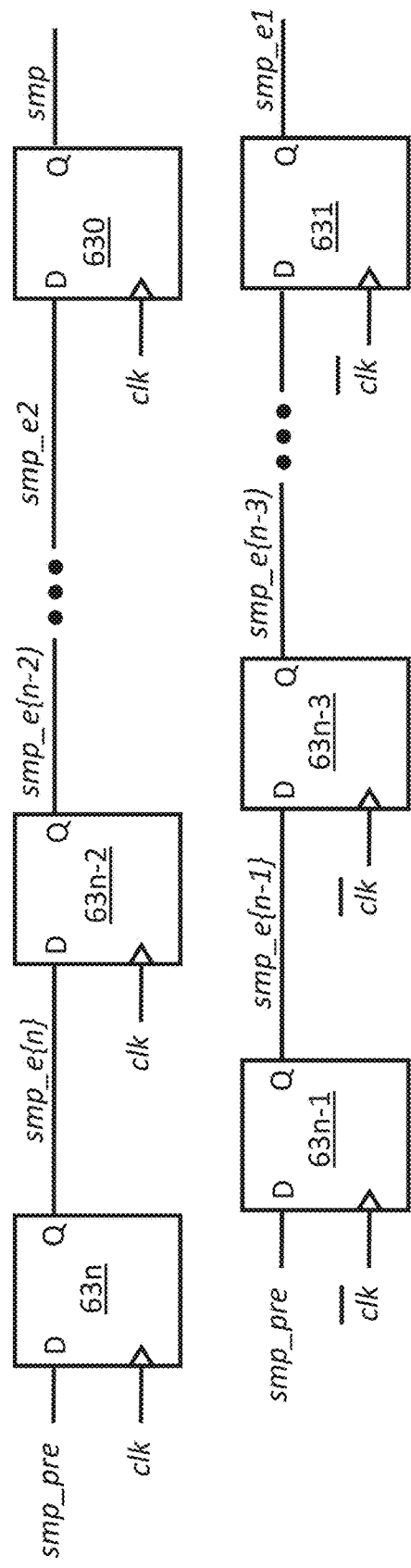
FIG. 6 illustrates another example of signal generation circuitry, in accordance with certain embodiments described herein.

FIG. 6 illustrates another example of signal generation circuitry, in accordance with certain embodiments described herein. FIG. 6 is a generic version of FIG. 5. In particular, FIG. 6 illustrates two series of flip-flops 63n, 63n-2 . . . 630 and 63n-1, 63n-3 . . . 631 to generate signals smp_e{n}, smp_e{n-2}, smp and smp_e{n-1}, smp_e{n-3}, smp_e1, respectively.

Figure 7:
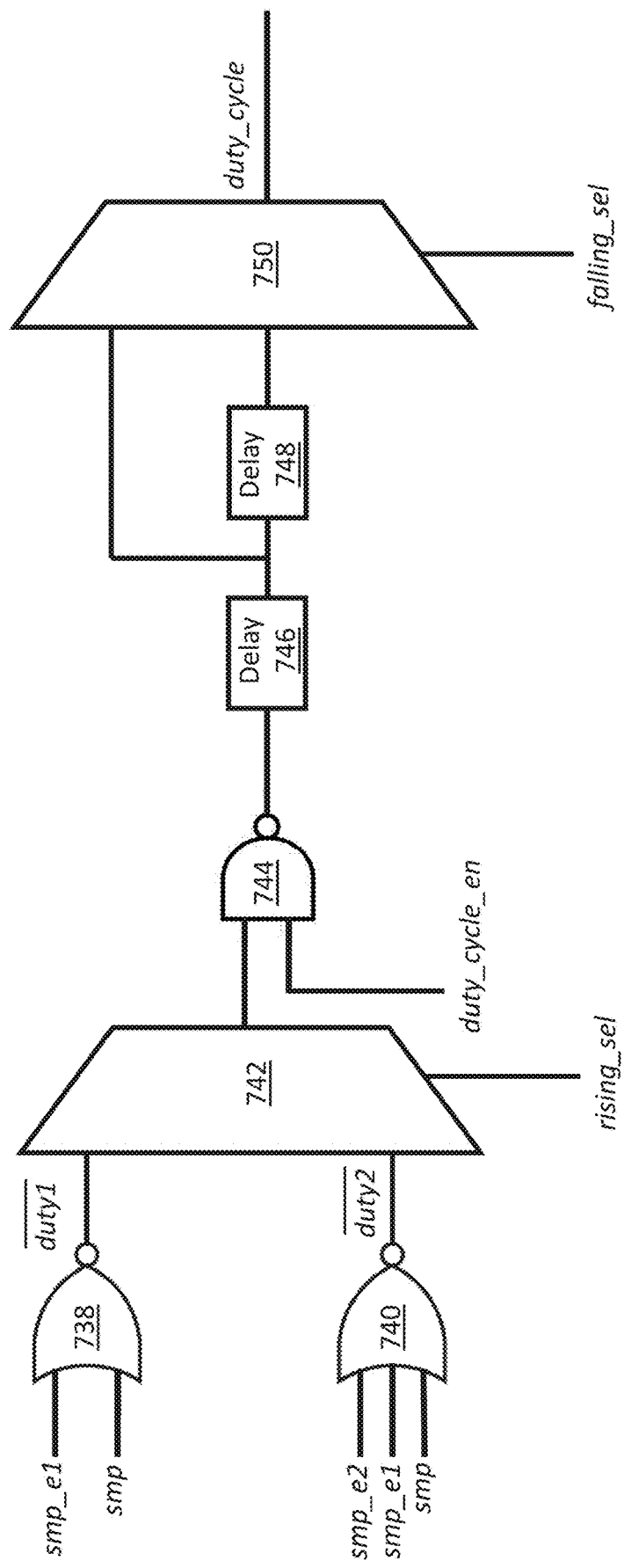
FIG. 7 illustrates another example of signal generation circuitry, in accordance with certain embodiments described herein.

FIG. 7 illustrates another example of signal generation circuitry, in accordance with certain embodiments described herein. FIG. 7 includes a NOR gate 738, a NOR gate 740, a multiplexer 742, a NAND gate 744, a delay block 746, a delay block 748, and a multiplexer 750. One input of the NOR gate 738 is coupled to smp_e1. The other input of the NOR gate 738 is coupled to smp. One input of the NOR gate 740 is coupled to smp_e2. Another input of the NOR gate 740 is coupled to smp_e1. The other input of the NOR gate 740 is coupled to smp. The output of the NOR gate 738, from which the inversion of the signal duty1 is taken, is coupled to one data input of the multiplexer 742. The output of the NOR gate 740, from which the inversion of the signal duty2 is taken, is coupled to the other data input of the multiplexer 742. A signal rising_sel is coupled to the select input of the multiplexer 742. The output of the multiplexer 742 is coupled to one input of the NAND gate 744. The other input of the NAND gate is coupled to a signal duty_cycle_en. The output of the NAND gate 744 is coupled to the input of the delay block 746. The output of the delay block 746 is coupled to the input of the delay block 748. The output of the delay block 746 is also coupled to one data input of the multiplexer 750. The output of the delay block 748 is coupled to another data input of the multiplexer 750. A signal falling_sel is coupled to the select input of the multiplexer 750. The signal duty_cycle is taken from the output of the multiplexer 750. The signals smp, smp_e1, and smp_e2 may be generated by the circuitry of FIG. 5 or FIG. 6. The signal duty_cycle generated by the circuitry in FIG. 7 may be the signal duty_cycle in FIG. 4.

In operation, the NOR gates 738 and 740 may generate two intermediate duty cycling signals, the inversions of duty1 and duty2, having different rising times. As illustrated in FIG. 8, these signals may differ by one-half clock cycle. The signal rising_sel may be used (e.g., programmed) to select either the inversion of duty1 or the inversion of duty2 at the output of the multiplexer 742 (i.e., to select a rising edge time). The signal duty_cycle_en may be used (e.g., programmed) to select whether duty cycling occurs. If duty_cycle_en is digital high, then the output of the NAND gate 744 may be the output of the multiplexer 742, namely an intermediate duty cycling signal, which may mean that duty cycling will occur. In such a case, the NAND gate 744 may also invert the inversions of duty1 or duty2 to produce either duty1 or duty2. If duty_cycle_en is digital low, then the output of the NAND gate 744 may be constant digital high, which may mean that duty cycling will not occur. Timing diagrams for duty1 and duty2 may be found in FIG. 8.

Assuming that the NAND gate 744 outputs an intermediate duty cycling signal duty1 or duty2, the delay block 746 may delay the intermediate duty cycling signal by one gate delay. The delay block 746 may delay the output of the delay block 746 by one gate delay, or in other words, delay the intermediate duty cycling signal duty1 or duty2 by two gate delays. The signal falling_sel may be used (e.g., programmed) to select either the intermediate duty cycling signal (which may be duty1 or duty2) delayed by one gate delay or the intermediate duty cycling signal delayed by two gate delays as the output duty_cycle, the final duty cycling signal.

Thus, the multiplexer 742 may be considered to control the rising edge time of the final duty cycling signal, and therefore may be considered to control $t_{driveron}$ in FIG. 4. While the delay blocks 746 and 748 may affect both the rising edge time and the falling edge time of the final duty cycling signal, the delays caused by the delay blocks 746 and 748 (on the order of a gate delay) may be significantly less than the difference in rising edge time controlled by the multiplexer 742 (on the order of one-half of a clock cycle). Thus, the multiplexer 750 may be considered to primarily control the falling edge time of the final duty cycling signal, and therefore may be considered to control $t_{driveroff}$ in FIG. 4. The difference between the possible falling edge times may be less than the difference between the possible rising edge times because the exact timing of the falling edge of duty_control may not be as critical as the timing of the rising edge, as long as the falling edge occurs later than the falling edge of smp.

FIG. 8 illustrates example timing diagrams for signals generated by signal generation circuitry, in accordance with certain embodiments described herein. FIG. 8 illustrates timing diagrams for clk and smp_pre (used by the circuitry in FIG. 5 or 6), smp_e2, smp_e1, and smp (generated by the circuitry in FIG. 5 or 6), and duty1 and duty2 (generated by the circuitry in FIG. 7). As described above, the circuitry of FIG. 7 may be used to select either duty1 or duty2, which may be equivalent to selecting a rising time, and also to select a falling time for whichever of duty1 or duty2 is selected. (The different falling time options for each of duty1 and duty2 are not shown in FIG. 8). The options for the final duty cycling signal may therefore include duty1 with falling time delayed by one gate delay, duty1 with falling time delayed by two gate delays, duty2 with falling time delayed by one gate delay, duty2 with falling time delayed by two gate delays, or a digital high signal (i.e., no duty cycling).

Figure 9:
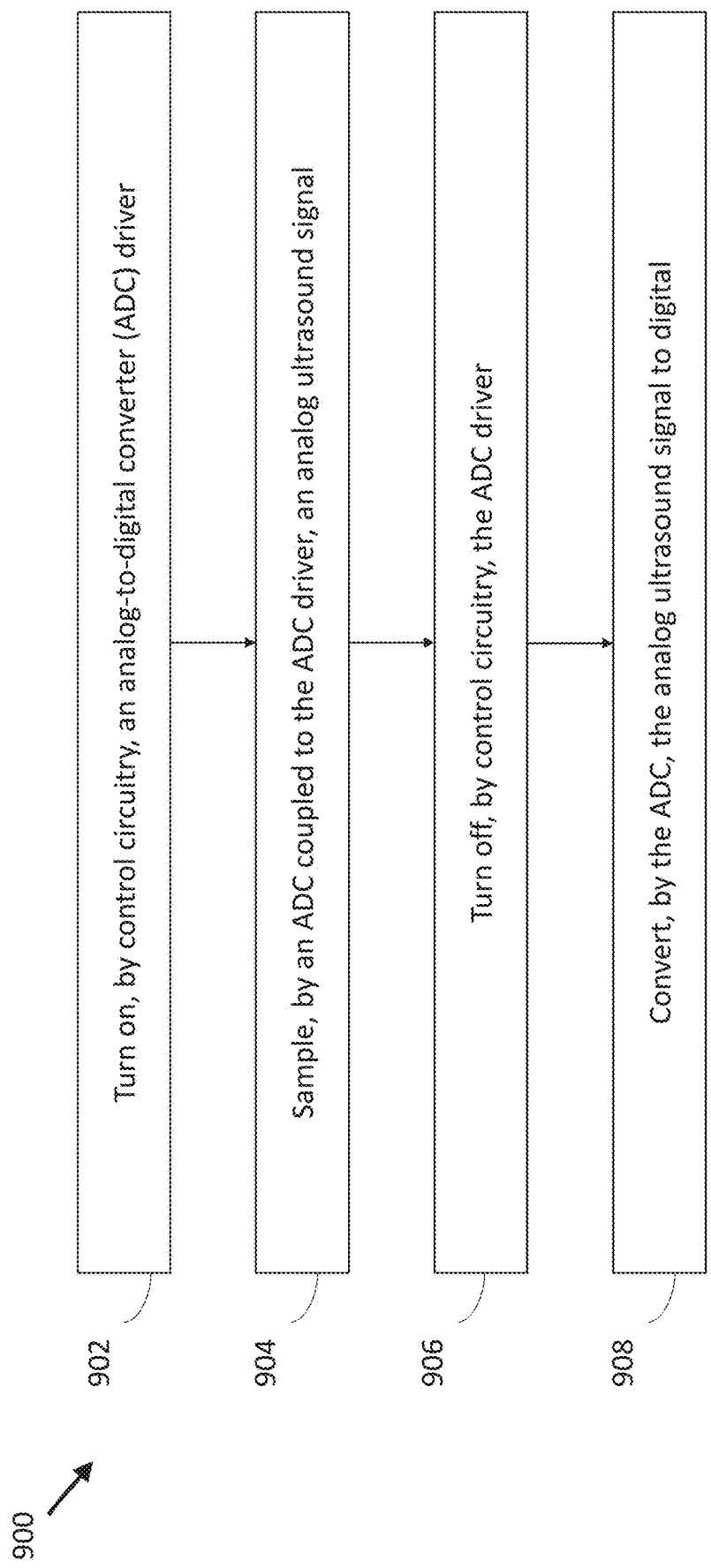
FIG. 9 illustrates an example process for processing ultrasound signals, in accordance with certain embodiments described herein.

FIG. 9 illustrates an example process 900 for processing ultrasound signals, in accordance with certain embodiments described herein. The process 900 is performed by an ultrasound device. For example, the ultrasound device may be an ultrasound-on-a-chip. The ultrasound device includes an ADC (e.g., the ADC 112), an ADC driver (e.g., the ADC driver 112) coupled to the ADC, and control circuitry coupled to the ADC driver. The ultrasound device may also include the circuitry described with reference to FIG. 1. The ADC driver may be configured to buffer analog ultrasound signals for outputting to the ADC. The ADC may be, for example, a successive approximation ADC configured to convert analog signals to digital signals. In some embodiments, the successive approximation ADC may be a charge-redistribution successive approximation ADC that includes a charge scaling digital-to-analog converter (DAC). The charge scaling DAC may include a large array of switchable binary-weighted capacitors all of which may be charged to the voltage of the input analog signal as part of the successive approximation ADC operation. Charging this capacitor array may require a large amount of current that may be provided by the ADC driver. Thus, the ADC driver may contribute significantly to power consumption of the ultrasound device. Turning on and off of the ADC driver (e.g., according to a duty cycle) with the process 900 may contribute to significantly decreasing the power consumption of the ultrasound device. Further description of the ADC driver may be found with reference to FIGS. 2-4.

In act 902, the control circuitry turns on the ADC driver. Turning on the ADC driver may include increasing the current flowing through the ADC driver (either from zero or from a non-zero current value). The control circuitry may be configured to output one or more signals (e.g., duty_cycle described above) controlling turning on and off of the ADC driver. In some embodiments, the ADC driver is an amplifier including transistors (e.g., the transistors 218-219) receiving input analog signals (e.g., the input signals vinp and vinn), current sources (e.g., the current sources 225-227) providing current to the transistors, and switches (e.g., the switches 221-224) coupled between the current sources and the transistors, such that the switches may be closed or opened to permit or prevent current to flow from the current sources to the transistors. Signal duty_cycle may control opening and closing of some or all of the switches in the ADC driver between the transistors receiving the input analog signals and the current sources. In some embodiments, the ADC driver may instead include transistors (e.g., the transistors 321-324) coupled between the current sources and the transistors, and the transistors may be turned on or off to permit or prevent current to flow from the current sources to the transistors. Signal duty_cycle (which may be generated as described in FIGS. 5-8) may control turning on and off transistors in the ADC driver between the transistors receiving the input analog signals and some or all of the current sources. The ADC may have a track phase when the ADC tracks (i.e., samples) the analog ultrasound signal inputted to the ADC, and a hold phase when the ADC converts the sampled analog ultrasound signal. In some embodiments, the ADC may be a successive approximation ADC. During the track phase, the ADC may couple the analog ultrasound signal to the capacitor array of a charge scaling DAC and charge the capacitor array to the analog ultrasound signal value. During the hold phase, the ADC may decouple the capacitor array from the analog ultrasound signal and convert the stored analog ultrasound signal value to digital.

The control circuitry may turn on the ADC driver at act 902 by switching duty_cycle. In some embodiments, the control circuitry may turn on the ADC driver a time period before the track phase. This may help the output of the ADC driver to settle (which may occur over a settling time period) prior to the track phase beginning, so that the analog ultrasound signal is accurately stored by the ADC prior to the end of the track phase. In some embodiments, if the length of the track phase is sufficiently long relative to the settling time of the ADC driver, the control circuitry may turn the ADC driver on after the track phase has begun, because the output of the ADC driver may still settle to a sufficient degree prior to the end of the track phase. The control circuitry may be configured to control the value of the on current by controlling bias circuitry. In particular, the control circuitry may be configured to output control signals to the bias circuitry to select how much current is supplied by current sources in the ADC driver. When the ADC driver turns on, the settling time of the ADC driver (in particular, the slew rate), and hence the bandwidth of the ADC driver, may depend on the on current. The bandwidth of the ADC driver may be controlled by enabling control circuitry to select a value for the on current from among multiple possible on current values. Providing more on current may decrease the settling time of the ADC driver more than if less current is provided, but result in the ADC driver consuming more power. The process 900 proceeds from act 902 to act 904.

In act 904, the ADC samples the analog ultrasound signal. This may occur during the track phase, as described above. The process 900 proceeds from act 904 to act 906.

In act 906, the control circuitry turns off the ADC driver. Turning on the ADC driver may include increasing the current flowing through the ADC driver (either from zero or from a non-zero current value). The control circuitry may turn off the ADC driver by switching duty_cycle. It should be appreciated that the ADC driver may buffer the analog ultrasound signal inputted to the ADC and provide large amounts of current to the ADC (e.g., to the capacitor array of a charge scaling DAC in the ADC) during the track phase, but not during the hold phase. Indeed, the ADC driver may not be needed for the hold phase. Accordingly, the ultrasound device may turn off the ADC driver during the hold phase. The control circuitry may turn off the ADC driver during the hold phase a time period $t_{driveroff}$ after the track phase has ended. This may help ensure that the turning off the ADC driver does not interfere with sampling of the analog ultrasound signal during the track phase (in act 904). Turning off the ADC driver may include reducing the current flowing through the ADC driver from the on current to an off current, which may be zero or a non-zero current. The value of the off current may depend on how much current, if any, control circuitry leaves flowing in the ADC driver when the ADC is turned off. When the current supplied to the ADC driver varies between on current ($I_{on}$) and off current ($I_{off}$), this may cause a disturbance in power supplied by the power supply. In particular, the change in dynamic current supplied to the ADC driver by the power supply may cause a voltage drop in the voltage provided by the power supply. The magnitude of this voltage drop may depend on $I_{on}$ and $I_{off}$. In particular, the voltage drop may be substantially equal to $(I_{on}-I_{off}) \times R_{mesh} - I_{on} (1-I_{off}/I_{on}) \times R_{mesh}$, where $R_{mesh}$ is the resistance of the power supply mesh. The power disturbance due to the ADC driver turning on and off may be controlled by enabling control circuitry to control selection of the off/on current ratio value (i.e., ($I_{off}/I_{on}$) from among multiple possible off/on current ratio values. The process 900 process from act 906 to act 908.

In act 908, the ADC converts the analog ultrasound signal to digital. This may occur during the hold phase, as described above.

It should be appreciated that ultrasound transducers and any of the circuitry illustrated in FIGS. 1-3 and 5-7 may be integrated on a single semiconductor chip or on multiple semiconductor chips in a stacked configuration.

Figure 10:
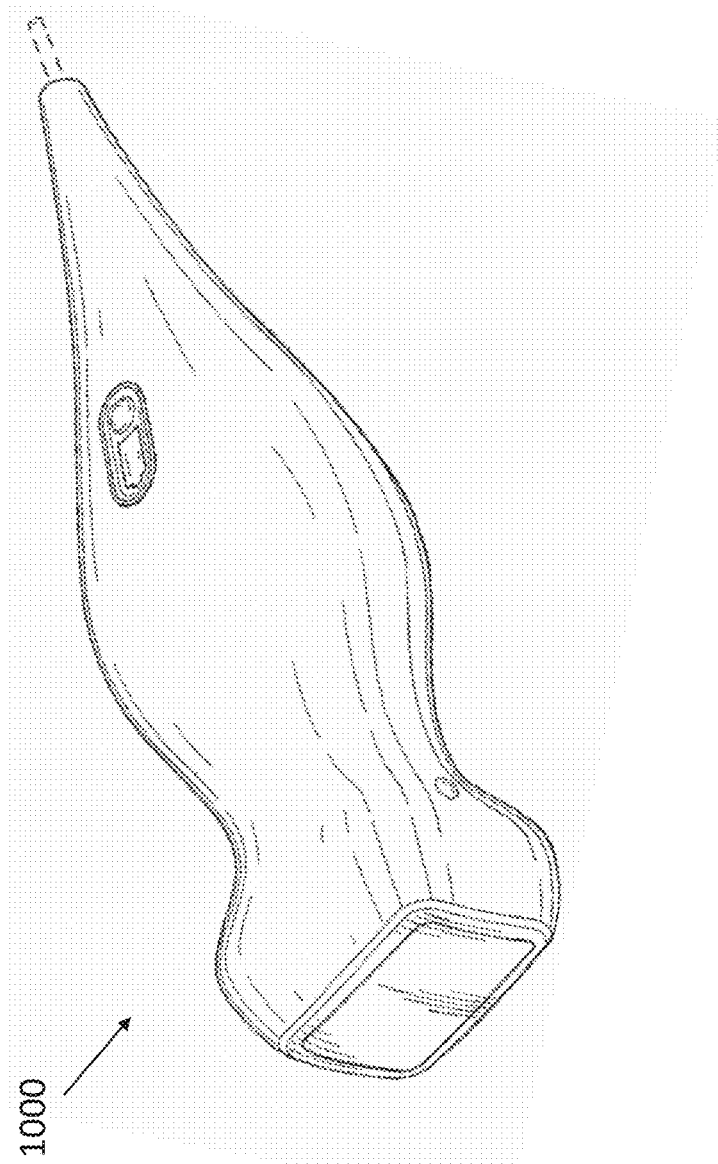
FIG. 10 illustrates an example handheld ultrasound probe, in accordance with certain embodiments described herein.

FIG. 10 illustrates an example handheld ultrasound probe 1000, in accordance with certain embodiments described herein. In some embodiments, an ultrasound-on-chip (e.g., the ultrasound-on-chip 100) including ultrasound transducers and any of the circuitry illustrated in FIGS. 1-3 and 5-7 may be integrated on this ultrasound-on-chip and disposed in the handheld ultrasound probe 1000.

Figure 11:
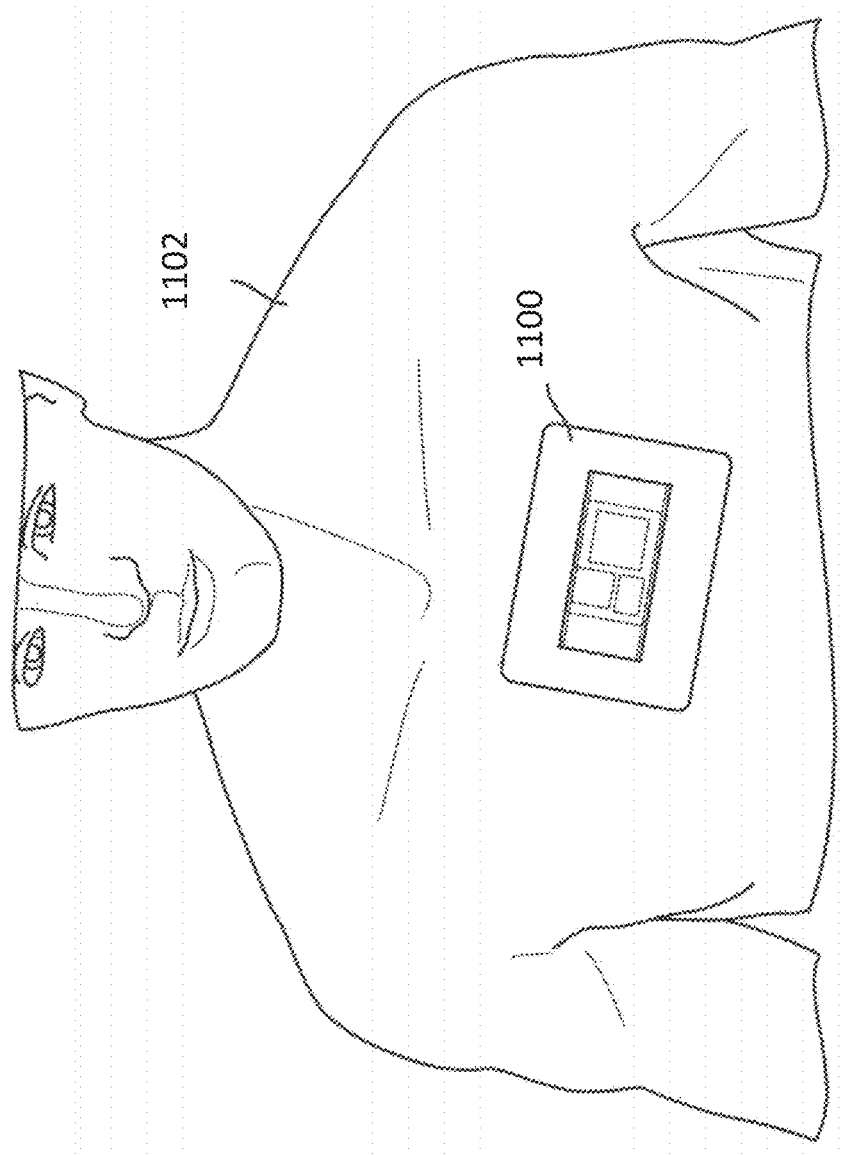
FIG. 11 illustrates an example wearable ultrasound patch, in accordance with certain embodiments described herein.

FIG. 11 illustrates an example wearable ultrasound patch 1100, in accordance with certain embodiments described herein. The wearable ultrasound patch 1100 is coupled to a subject 1102. In some embodiments, an ultrasound-on-chip (e.g., the ultrasound-on-chip 100) including ultrasound transducers and any of the circuitry illustrated in FIGS. 1-3 and 5-7 may be integrated on this ultrasound-on-chip and disposed in the wearable ultrasound patch 1100.

Figure 12:
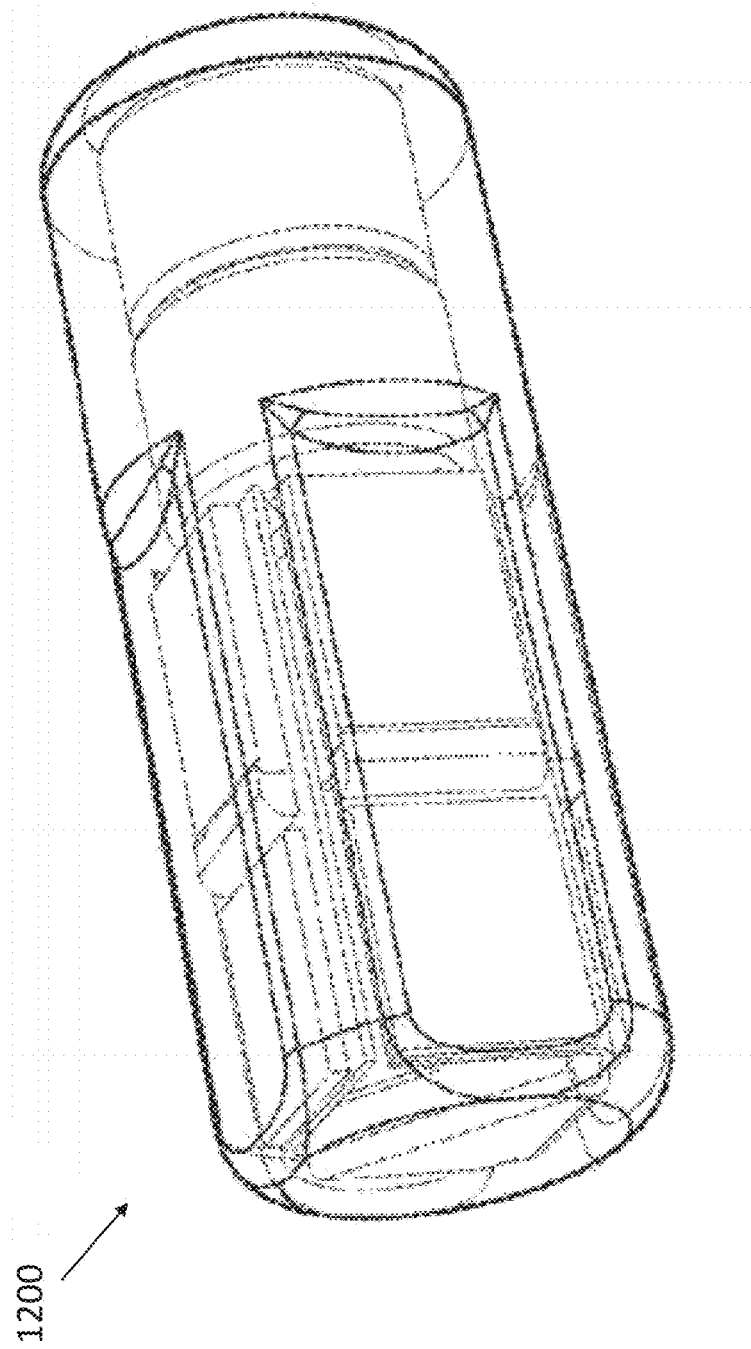
FIG. 12 illustrates an example ingestible ultrasound pill, in accordance with certain embodiments described herein.

FIG. 12 illustrates an example ingestible ultrasound pill 1200, in accordance with certain embodiments described herein. In some embodiments, an ultrasound-on-chip (e.g., the ultrasound-on-chip 100) including ultrasound transducers and any of the circuitry illustrated in FIGS. 1-3 and 5-7 may be integrated on this ultrasound-on-chip and disposed in the ingestible ultrasound pill 1200.

Further description of the handheld ultrasound probe 1000, the wearable ultrasound patch 1100, and the ingestible ultrasound pill 1200 may be found in U.S. patent application Ser. No. 15/626,711 titled "UNIVERSAL ULTRASOUND IMAGING DEVICE AND RELATED APPARATUS AND METHODS," filed on Jun. 19, 2017 and published as U.S. Pat. App. Publication No. 2017-0360399 A1 (and assigned to the assignee of the instant application).

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound device, comprising:
control circuitry; and
an analog-to-digital converter (ADC) driver coupled to the control circuitry;
wherein the control circuitry is configured to:
turn on and off the ADC driver; and
control a ratio between a current in the ADC driver when the ADC driver is turned off and a current in the ADC driver when the ADC driver is turned on.

2. The ultrasound device of claim 1, wherein the control circuitry is configured to turn on and off the ADC driver in synchronization with sampling activity of an ADC.

3. The ultrasound device of claim 1, wherein the control circuitry is configured to turn on and off the ADC driver based on when an ADC is sampling.

4. The ultrasound device of claim 1, wherein the control circuitry is configured to control a duty cycle of the ADC driver turning on and off.

5. The ultrasound device of claim 4, wherein the control circuitry is configured to control the duty cycle of the ADC driver turning on and off by selecting a duty cycle value from among multiple possible duty cycle values.

6. The ultrasound device of claim 5, where the multiple possible duty cycle values comprise three or more possible duty cycle values.

7. The ultrasound device of claim 1, wherein the control circuitry is configured to control the ratio between the current in the ADC driver when the ADC driver is turned off and the current in the ADC driver when the ADC driver is turned on by selecting the ratio from among multiple possible ratio values.

8. The ultrasound device of claim 7, where the multiple possible ratio values comprise three or more possible ratio values.

9. The ultrasound device of claim 1, wherein the control circuitry is configured to control a value of a current in the ADC driver when the ADC driver is turned on.

10. The ultrasound device of claim 1, wherein the control circuitry is configured to control a value of a current in the ADC driver when the ADC driver is turned off.

11. The ultrasound device of claim 10, wherein the control circuitry is configured to control the value of the current in the ADC driver when the ADC driver is turned off by selecting the value from among multiple possible values.

12. The ultrasound device of claim 11, where the multiple possible values comprise three or more possible values.

13. The ultrasound device of claim 1, wherein the ADC driver comprises:
   a transistor receiving an input analog signal;
   a current source; and
   a switch coupled between the transistor and the current source;
   wherein the control circuitry is configured to turn off the ADC driver by opening the switch.

14. The ultrasound device of claim 1, wherein the ADC driver comprises:
   a transistor receiving an input analog signal;
   a first current source;
   a second current source;
   a first switch coupled between the transistor and the first current source; and
   a second switch coupled between the transistor and the second current source;
   wherein the control circuitry is configured to turn off the ADC driver by opening either the first switch, the second switch, or both the first and second switches.

15. The ultrasound device of claim 1, wherein the ADC driver comprises:
   a first transistor receiving an input analog signal;
   a current source; and
   a second transistor coupled between the first transistor and the current source;
   wherein the control circuitry is configured to turn off the ADC driver by turning off the second transistor.

16. The ultrasound device of claim 1, wherein the ADC driver comprises:
   a first transistor receiving an input analog signal;
   a first current source;
   a second current source;
   a second transistor coupled between the first transistor and the first current source; and
   a third transistor coupled between the first transistor and the second current source;
   wherein the control circuitry is configured to turn off the ADC driver by turning off the second transistor, the third transistor, or both the second and third transistors.

17. The ultrasound device of claim 16, wherein the control circuitry is configured to turn off the second transistor, the third transistor, or both the second and third transistors by switching a signal at a gate of the second transistor, the third transistor, or both the second and third transistors from high to low or from low to high.

18. The ultrasound device of claim 1, further comprising:
   an ADC coupled to an output of the ADC driver and configured to:
      sample an analog ultrasound signal; and
      convert the analog ultrasound signal to digital subsequent to sampling the analog ultrasound signal;
   wherein the control circuitry is configured to turn on and off the ADC driver by turning on the ADC driver prior to the ADC sampling the analog ultrasound signal and to turn off the ADC driver prior to the ADC converting the analog ultrasound signal.

19. An ultrasound device, comprising:
control circuitry;
an analog-to-digital converter (ADC) driver coupled to the control circuitry;
wherein the control circuitry is configured to turn on and off the ADC driver;
an ADC coupled to an output of the ADC driver and configured to operate with a track phase and a hold phase; and
wherein the control circuitry is configured to turn on and off the ADC driver by turning on the ADC driver during the hold phase a first time period before the track phase and by turning off the ADC driver during the hold phase a second time period after the track phase.

20. The ultrasound device of claim 1, wherein the ultrasound device comprises an ultrasound-on-chip.

* * * * *